(12) United States Patent
Biagini et al.

(10) Patent No.: US 8,198,497 B2
(45) Date of Patent: Jun. 12, 2012

(54) CATALYTIC COMPOSITION AND PROCESS FOR THE SELECTIVE OLIGOMERIZATION OF ETHYLENE TO LIGHT LINEAR ALPHA-OLEFINS

(75) Inventors: Paolo Biagini, Trecate (IT); Liliana Gila, Cameriano-Casalino (IT)

(73) Assignee: Polimeri Europa S.p.A., Brindisi (IT)

( * ) Notice: Subject to any disclaimer, the term of this patent is extended or adjusted under 35 U.S.C. 154(b) by 654 days.

(21) Appl. No.: 10/497,537

(22) PCT Filed: Dec. 9, 2002

(86) PCT No.: PCT/EP02/13957
§ 371 (c)(1),
(2), (4) Date: Nov. 9, 2004

(87) PCT Pub. No.: WO03/053573
PCT Pub. Date: Jul. 30, 2003

(65) Prior Publication Data
US 2005/0070425 A1  Mar. 31, 2005

(30) Foreign Application Priority Data
Dec. 13, 2001 (IT) ............................... MI2001A2629

(51) Int. Cl.
*C07C 2/22* (2006.01)
(52) U.S. Cl. ........ 585/513; 585/502; 585/510; 585/511; 585/512; 585/520; 585/521; 585/522; 585/523; 585/526
(58) Field of Classification Search .................. 585/513, 585/515, 526, 527, 502, 510, 511, 512, 520, 585/521, 522, 523, 532; 502/103, 122
See application file for complete search history.

(56) References Cited

U.S. PATENT DOCUMENTS

| | | | |
|---|---|---|---|
| 3,652,705 A * | 3/1972 | Arakawa et al. | 585/522 |
| 3,660,519 A * | 5/1972 | Arakawa et al. | 585/524 |
| 3,932,550 A | 1/1976 | Morikawa et al. | |
| 4,147,664 A | 4/1979 | Pomogailo et al. | |
| 4,243,782 A * | 1/1981 | Bye et al. | 526/140 |
| 4,336,360 A | 6/1982 | Giannini et al. | |
| 4,486,615 A * | 12/1984 | Langer, Jr. | 585/523 |
| 4,783,573 A * | 11/1988 | Shiraki et al. | 585/523 |
| 4,966,874 A * | 10/1990 | Young et al. | 502/117 |
| 5,043,515 A * | 8/1991 | Slaugh et al. | 585/512 |
| 5,260,500 A * | 11/1993 | Shiraki et al. | 585/524 |
| 5,292,979 A * | 3/1994 | Chauvin et al. | 585/523 |
| 5,461,127 A * | 10/1995 | Naganuma et al. | 526/127 |

FOREIGN PATENT DOCUMENTS

| | | |
|---|---|---|
| GB | 1 274 114 | 5/1972 |
| GB | 1 553 103 | 9/1979 |

* cited by examiner

*Primary Examiner* — In Suk Bullock
*Assistant Examiner* — Bradley Etherton
(74) *Attorney, Agent, or Firm* — Oblon, Spivak, McClelland, Maier & Neustadt, L.L.P.

(57) ABSTRACT

A catalytic composition for the selective oligomerization of ethylene and a process for preparing light linear (α-olefins, especially 1-hexene and 1-octene, starting from ethylene, using this composition, said composition comprising the following components: (A) a compound of a transition metal M of Group 4 of the periodic table; (B) an organic compound containing the sulfonic group ($>SO_2$) bonded to two carbon atoms; (C) a hydrocarbyl organometallic compound of a metal M' selected from elements of Groups 1, 2, 12, 13 or 14 of the periodic table; components (A), (B) and (C) being in such a quantity that the atomic ratios respectively of the metal M in (A), of the sulfur S in the sulfonic group of (B) and of the metal M' in (C), respect the following proportions: S/M= (from 0 to 20)/1 and M'/M=(from 2 to 2000)/1, on the condition that when the compound of the metal M in component (A) is not a sulfonic complex of M, the S/M ratio is greater than 0.5, preferably greater than 1.

25 Claims, No Drawings

CATALYTIC COMPOSITION AND PROCESS FOR THE SELECTIVE OLIGOMERIZATION OF ETHYLENE TO LIGHT LINEAR ALPHA-OLEFINS

The present invention relates to a catalytic system comprising sulfonic compounds, which can be used in processes for the selective oligomerization of ethylene to light linear α-olefins.

Linear α-olefins represent an important petrochemical material. Their applications, depending on the number of carbon atoms, range from their use as comonomers in the production of polyethylenes, their use as plasticizers and synthetic lubricants, to their use as intermediates in the production of detergent alcohols. In particular, linear α-olefins having from 4 to 8 carbon atoms are widely used as comonomers for the production of polyethylenes with varying degrees of density and crystallinity, particularly suitable for producing end-products by means of filming and injection moulding processes.

The possible oligomerization of ethylene to 1-hexene, 1-octene and also 1-butene, seems to be an interesting synthesis method due to the great demand for these monomers.

According to U.S. Pat. No. 3,644,563 (Shell), homogeneous catalysts based on organometallic complexes of nickel comprising a bidentate ligand (P—O) on which the catalytic activity and selectivity depend, are used for oligomerizing ethylene. The catalytic precursor is prepared at 40° C. by the reaction of $NiCl_2$ and said bidentate ligand P—O (such as for example diphenylphosphino acetic acid and diphenylphosphino benzoic acid) in the presence of ethylene and a reducing agent, such as $NaBH_4$. The oligomerization, on the other hand, is carried out at 120° C. and 14 MPa (140 bar). The olefins obtained according to this process have a high linearity and their molecular weights follow a Shulz Flory distribution.

The process therefore has the disadvantage of requiring rather drastic pressure and temperature conditions, and of giving a wide distribution of α-olefins.

U.S. Pat. No. 4,783,573 (Idemitsu) describes a process in which ethylene is oligomerized at 3.5 MPa and 120° C., in the presence of a catalytic system which comprises $ZrCl_4$, aluminum alkyls and a Lewis base which can be selected from various groups of organic compounds containing heteroatoms, such as alkyldisulfides, thioethers, thiophenes, phosphines and primary amines. The olefins obtained are mainly $C_4$-$C_8$ but considerable quantities of heavy olefins are still present and their preparation moreover also requires high temperatures and pressures.

EP-A-681,106 (Phillips) describes catalytic systems based on chromium(III)alkanoates, which are generally activated with aluminum alkyl $AlEt_3$ mixed with $AlClEt_2$, in the presence of a pyrrole, or one of its alkaline salts, and a halogenating agent, preferably $GeCl_4$, used at temperatures of about 100° C. with ethylene pressures higher than 40 atm. These chromium catalytic systems produce 1-hexene with a selectivity of over 99% and a high activity only at a high ethylene pressure, as polyethylene is obtained at low pressures.

International patent application WO 92/10446 (Institut Française du Petrol) describes a process for converting ethylene to linear α-olefins in the presence of a catalyst consisting of a zirconium alcoholate, an aluminum chloro-alkyl and an ether. Although the catalyst is active under relatively bland conditions, neither the selectivity of the process towards olefins having 4, 6 and 8 carbon atoms nor the distribution of the product among these compounds, which is too much orientated towards the production of 1-butene, are satisfactory.

The Applicant has now surprisingly found that a composition comprising certain compounds of light transition metals combined with sulfonic compounds is capable of catalyzing the oligomerization reaction of ethylene towards the elective production of 1-hexene and 1-octene, thus substantially overcoming the drawbacks specified above.

In accordance with this, a first object of the present invention relates to a catalytic composition which can be used for the selective oligomerization of ethylene to give linear α-olefins, comprising the following components:
(A) at least one compound of a transition metal M of Group 4 of the periodic table;
(B) at least one organic compound containing at least one sulfonic group ($>SO_2$) bonded to two carbon atoms;
(C) at least one hydrocarbyl organometallic compound of a metal M' selected from elements of Groups 1, 2, 12, 13 or 14 of the periodic table;

the components (A), (B) and (C) being in such a quantity that the atomic ratios respectively of the metal M in (A), of the sulfur S in the sulfonic group of (B) and of the metal M' in (C), respect the following proportions:

$S/M = (\text{from 0 to 20})/1$ $M'/M = (\text{from 2 to 2000})/1,$ on the condition that when the compound of the metal M in component (A) is not a sulfonic complex of M, the S/M ratio is greater than 0.5, preferably greater than 1.

Another object of the present invention relates to a process for the oligomerization of ethylene to prevalently form linear α-olefins having 4, 6 or 8 carbon atoms, which comprises reacting ethylene under oligomerization conditions in the presence of the above catalytic composition.

Other objects of the present invention are evident from the following description and claims.

The term "composition", as used in the present description and claims should be considered as referring not only to any aggregation form of the components, regardless of whether they are in contact with each other or not, but also any product or mixture of products which can be formed by chemical reaction or physico-chemical interaction with each other, optionally also in the presence of other components not specified.

Component (A) of the catalytic composition according to the present invention can consist of any suitable organic or inorganic compound of a metal M of Group 4 of the periodic table of elements (as published in "The IUPAC Red Book, Nomenclature of Inorganic Chemistry", Blackwell Science Ed., 1990, to which reference is made in the present description with the term "periodic table"), preferably having an oxidation state +4, although lower oxidation states, especially +3, are also included in the scope of the present invention.

The metal M is preferably titanium or zirconium, more preferably zirconium. Mixtures of several compounds of one or more metals of group 4 of the periodic table are however included in the definition of component (A) of the above catalytic composition as claimed herein.

For the purposes of the present invention, it is not necessary for said compound of the metal M in component (A) to be soluble in the organic solvents commonly used, as can be observed hereafter, in the preparation of the catalytic composition, as it can also be used in solid form or as a suitable suspension. Compounds of M soluble in suitable inert solvents are however preferred.

According to a particular preferred aspect, the metallic compound in component (A) has the following formula (I):

$$[MX_1X_2X_3(X_4)_nY_m]_s \qquad (I)$$

wherein:
M is a metal selected from metals of Group 4 of the periodic table in oxidation state 3 or 4, preferably titanium or zirconium, more preferably zirconium;

$X_1$, $X_2$, $X_3$ and $X_4$ each independently represent any organic or inorganic ligand of an anionic nature, bonded to the metal M as anion in an ionic couple or with a covalent bond;

each Y represents a neutral organic ligand coordinated to the metal M by means of at least one heteroatom selected from non-metallic atoms of groups 15 or 16 of the periodic table, "n" has the values of 0 or 1 respectively, if the oxidation state of the metal M is 3 or 4, and is preferably 1;

"m" represents the number of neutral ligands Y optionally coordinated to M and can have any integer or decimal value ranging from 0 to 3, extremes included, preferably from 0 to 2, and "s" has integer values ranging from 1 to 6, preferably from 1 to 2, extremes included.

The compound having formula (I) according to the present invention can be of a monomeric (s=1), dimeric (s=2) or polynuclear (s ranging from 3 to 6) form, or it may macroscopically consist of any mixture of molecules having formula (I) with the index "s" varying from 1 to 6. It has been found in fact that, depending on the nature of the ligands X, the metal M, the neutral ligands Y, as well as the physical state of the compound having formula (I), depending on whether it is liquid, solid or in solution, various molecular aggregation forms such as monomeric or dimeric, are possible, comprising, in certain cases, one or more Y ligands bridge-bonded between the two metals M.

The metal M in formula (I) is preferably titanium or zirconium.

Each of the ligands X (i.e. $X_1$, $X_2$, $X_3$ or $X_4$) independently represents any group of an anionic nature suitable for at least partially neutralizing the oxidation state of M, and can be organic or inorganic, preferably comprising from 1 to 30 atoms different from hydrogen. When X is organic, it preferably comprises from 1 to 30, more preferably from 1 to 10, carbon atoms.

Ligands X ($X_1$, $X_2$, $X_3$ or $X_4$) are, for example, halides, especially chlorides and bromides, the hydroxide group, hydrogen-carbonate group, nitrates or nitrites, $-NR_1R_2$ amide or $-PR_1R_2$ phosphide groups, wherein $R_1$ and $R_2$ are each hydrogen or an alkyl or aryl group preferably having from 1 to 20 carbon atoms, optionally bonded to each other to form a cyclic structure comprising the nitrogen or phosphorus atom, linear or branched alkoxide groups, preferably having from 1 to 10 carbon atoms, groups deriving from organic acids, such as carboxylate, carbamate or xanthate, preferably having from 1 to 10 carbon atoms, linear or branched alkyl-sulfide groups, linear, cyclic or branched hydrocarbyl groups, especially alkyl or aryl, preferably having from 1 to 15 carbon atoms, optionally also comprising one or more halogen atoms, especially chlorine and fluorine, and all other groups of an anionic nature generally suitable, as far as is known in the art, for the formation of compounds and complexes with metals in a positive oxidation state, also including groups bonded to the metal M with bonds of the "π" or mixed "σ" and "π" type, such as, for example, cyclopentadienyl or allyl hydrocarbyl groups, and groups deriving from diketonates or ketoesters, such as, for example, ethylacetylacetate or acetylacetonate groups, all preferably having up to 15 carbon atoms.

Furthermore, according to the present invention, two or more of the above ligands $X_1$, $X_2$, $X_3$ or $X_4$ can be aggregated with each other to represent a polyvalent ligand, especially divalent, such as, for example, oxide, carbonate, sulfate, phosphate and, among the organic groups, all poly-functional anionic groups containing two or more suitable functions in the molecule selected from those characteristic of the anionic groups mentioned above, such as, for example, amide, phosphide, alkoxide, carboxylate, carbamate, xanthate, sulfide, carbyl functions, including allyl, cyclopentadienyl, β-ketoesterate and β-diketonate groups.

Typical examples of X ($X_1$, $X_2$, $X_3$ or $X_4$) groups suitable for the purposes of the present invention are: fluoride, chloride, bromide, iodide, dimethyl-amide, dibutyl-amide, diphenyl-amide, bis(trimethylsilyl)-amide, dimethyl-phosphide, diphenyl-phosphide, methoxide, ethoxide, iso-propoxide, butoxide, ter-butoxide, phenoxide, 2,6-di-ter-butylphenoxide, p-fluorophenoxide, pentafluorophenoxide, acetate, propionate, 2-ethylhexanoate, versatate, naphthenate, benzoate, N,N-diethyl-carbamate, N,N-dibutyl-carbamate, N,N-di-isopropyl-carbamate, N,N-dicyclohexyl-carbamate, N,N-diphenylcarbamate, hydride, methyl, ter-butyl, neopentyl, phenyl, benzyl, p-fluorophenyl, pentafluorophenyl. Chloride, $C_1$-$C_8$ alkoxide and $C_2$-$C_{12}$ carboxy-late, ligands are particularly preferred for their commercial availability and solubility in solvents commonly used in the preparation of the above complexes and processes catalyzed thereby.

Y groups suitable for the purposes of the present invention are generally all neutral organic compounds having a coordinating capacity. Compounds of metals of Group 4, both trivalent and tetravalent, coordinated with one or more neutral organic groups, are known and described in literature relating to organometallic chemistry and the oligo- and poly-merization catalysis of olefins. The Y groups are preferably organic compounds having from 1 to 30 carbon atoms and containing from 1 to 8, preferably from 1 to 5 atoms selected from N, P, O and S. These groups can be selected, for example, from the groups of amines, especially tertiary, nitrites, isonitriles, ethers, thioethers, phosphines, phosphites, phosphine-oxides, ketones, aldehydes, esters, organic carbonates such as diethylcarbonate, sulfoxides, sulfones.

According to a preferred embodiment of the present invention, said component (A) comprises at least one compound having formula (I) wherein Y is absent (m=0), or it is a sulfonic compound or labile coordinating compound which can be substituted by contact and reaction with a sulfonic compound. Labile coordinating compounds are, for example, certain fluorinated ethers such as pentafluoroanisole or pentafluoropropyleneoxide, or certain fluorinated pyridines such as pentafluoropyridine.

Said Y group is more preferably a sulfonic compound (or sulfone), i.e. an organic compound comprising the $>SO_2$ group bonded to two carbon atoms and coordinated to the metal M by means of at least one oxygen atom.

Preferred sulfonic compounds according to this aspect of the present invention are represented by means of the following formula (II):

(II)

wherein $R_3$ and $R_4$, the same or different, each independently represent a linear or branched, saturated or unsaturated, cycloaliphatic or aromatic $C_1$-$C_{20}$, preferably $C_1$-$C_{10}$, hydrocarbyl group, or a $C_1$-$C_{20}$, preferably $C_1$-$C_{10}$, hydrocarbyl group substituted with one or more halogen atoms, or a $C_1$-$C_{20}$, preferably $C_1$-$C_{10}$, hydrocarbyl group comprising one or more heteroatoms of Groups 14 to 16 of the periodic table of elements, preferably Si, O, N, S, P, furthermore, $R_3$ and $R_4$ can be joined to each other to form a saturated or unsaturated, $C_4$-$C_{20}$ cyclic structure, comprising the sulfur atom of the sulfonic group, said structure optionally containing one or more of the heteroatoms indicated above.

Typical examples of sulfonic compounds having general formula (II) are: dimethylsulfone, diethylsulfone, dibutylsulfone, dicyclohexylsulfone, diphenylsulfone, bis(p-methylphenyl)sulfone, bis(p-chlorophenyl)sulfone, bis(p-fluorophenyl)sulfone, bis(pentafluorophenyl)sulfone, bis-(2,4,6-trimethylphenyl)-sulfone, methylphenylsulfone, butylphenylsulfone, tetrahydrothiophene-1,1-dioxide (also known as sulfolane), 3-sulfolene (2,5-dihydrothiophene-1,1-dioxide), 2,4-dimethyl sulfolane (2,4-dimethyltetra-hydrothiophene-1,1-dioxide), 1-(methylsulfonyl)pyrrole, 2-(methylsulfonyl)benzothioazole, 1-(phenylsulfonyl)indole, 1-(phenylsulfonyl)pyrrole, 2-(phenylsulfonyl)tetrahydro-pyrane.

When Y above represents a sulfonic group, the Applicant has also found that the catalytic composition in question can consist of components (A) and (C) alone, component (B) in this case being optional, i.e. that the S/M ratio between the sulfonic sulfur in component (B) and the metal M in component (A) can be either 0 or greater than 0. In this case in fact, the advantageous function of the sulfonic group in component (B) is substantially substituted by the sulfonic group already present in the compound having formula (I) of component (A).

Catalytic compositions comprising, as component (A), a sulfonic compound of the metal M and a further quantity of sulfonic compound, the same as or different from that included in (A), as component (B), and consequently with a S/M ratio greater than 0, are possible however and are included in the scope of the present invention.

In the above formula (I) the suffix "n" can have values of 0 or 1. In the preferred case of tetravalent M, "n" has the value of 1. When "n" is 0, the ligand $X_4$ is not present in the complex having formula (I) and the metal M has oxidation state +3.

The suffix "s" represents the molecular aggregation level of the compounds having formula (I). It can have any integer value up to 6, depending on the nature of the metal and of the ligands X and Y, the physical state and, for compounds having formula (I) in solution, depending on the solvent. More commonly, the compounds having formula (I) are in the form of a monomer or dimer, with "s" equal to 1 or 2 respectively.

The suffix "m" in the above formula (I) indicates the average number of sulfonic ligands Y, also optionally different from each other, bonded to each metallic centre M. As described above, in the case of certain di- or poly-nuclear complexes having formula (I), it has been found that a ligand Y can form a bridge between two metallic centers, thus determining a non-integer "m" index, for example having a value of 1.5.

The compounds having formula (I) are generally known in literature and many of them are easily available commercial products. For non-commercial compounds, the relative preparation methods are generally described in specific literature.

Typical examples of compounds having formula (I) are: titanium tetrachloride, zirconium tetrachloride, zirconium tetrachloridemonodiethylether, titanium tetrachloride bis-tetrahydrofuran, zirconium tetrachloride bis-tetrahydrofuran, hafnium tetrachloride bis-tetrahydrofuran, zirconium tetrachloride bis-benzaldehyde, zirconium tetrachloride bis-acetone, zirconium tetrachloride bis-acetophenone, zirconium tetrachloride bis-benzophenone, zirconium tetrachloride ethyl mono-formiate, zirconium tetrachloride dodecyl mono-formiate, zirconium tetrachloride ethyl mono-acetate, zirconium tetrachloride ethyl mono-ethylhexanoate, zirconium tetrachloride butyl mono-benzoate, titanium tetrachloride bis-pyridine, zirconium tetrachloride bis-pyridine, hafnium tetrachloride bis-pyridine, zirconium tetrachloride bis-benzoquinoline, zirconium tetrachloride mono-dipyridyl, zirconium tetrachloride mono-1,10-phenanthroline, zirconium tetrachloride bis-trimethylamine, titanium tetrachloride bis-trimethylamine, zirconium tetrabromide bis-trimethylamine, hafnium tetrachloride bis-triethylamine, zirconium tetrabromide, zirconium tetraiodide, hafnium tetrachloride, titanium tetra-ethoxide, titanium tetrabutoxide, zirconium tetra-ethoxide, zirconium tetrabutoxide, zirconium diacetatedichloride, titanium diacetylacetonatedichloride, zirconium diacetylacetonatedichloride, hafnium diacetylacetonatedichloride, zirconium tetra-acetylacetonate, hafnium tetra-acetylacetonate, zirconium tetra-allyl, titanium tetrabenzyl, zirconium tetrabenzyl, zirconium tetracyclopentadienyl, hafnium tetracyclopentadienyl, zirconium bis-cyclopentadienyl dichloride, titanium bis-indenyl dichloride.

The complexes having formula (I) with Y groups consisting of sulfonic compounds are less known. The complex $[TiCl_4(sulfolane)]_2$ was publicly made known on the occasion of the meeting "Trends in transition metal chemistry: towards the third millennium" 24-27 Feb. 2000, Pisa (Italy), without mentioning however any industrial use thereof.

Sulfonic complexes having formula (I) can be obtained with the known techniques for the preparation of transition metal complexes and are easily formed by the simple contact in a solution and/or suspension of an inert solvent, preferably a hydrocarbon or halogenated hydrocarbon, between a suitable precursor compound having the formula $MX_1X_2X_3(X_4)_n$ (in which the various symbols have the same meaning as the corresponding symbols of formula (I)) and the desired sulfonic compound, preferably selected from those having general formula (II).

According to a typical preparation method of said sulfonic complexes having formula (I), the pre-selected sulfonic compound (II), pure or diluted in a hydrocarbon solvent, optionally halogenated, such as for example, pentane, hexane, benzene, toluene, chlorobenzene, methylene chloride, tetrachloro ethane, preferably toluene, methylene chloride, even more preferably methylene chloride, is generally slowly added to a stirred mixture, comprising the precursor compound having the formula $MX_1X_2X_3(X_4)_n$ and a solvent selected from those mentioned above, preferably the same solvent in which the sulfonic compound (II) is diluted. There are no particular temperature limitations for carrying out the formation reaction of the complex having formula (I), but it is preferable to use a temperature ranging from −30° to 70° C., even more preferably room temperature, for the obvious sake of simplicity. The complexing reaction between the sulfonic compound Y and the precursor $MX_1X_2X_3(X_4)_n$ is weakly exothermic and generally does not create any problems relating to the disposal of the reaction heat.

The stoichiometric ratio between the sulfonic compound Y and the precursor $MX_1X_2X_3(X_4)_n$ determines the type of complex having formula (I) obtained, for example using a molar ratio $[Y]/[MX_1X_2X_3(X_4)_n]$ equal to 1, complexes having formula (I) are obtained in which "m" is equal to 1 and "s" is commonly equal to 2; whereas if the same molar ratio is raised to 2, complexes (I) are produced, in which "m" is usually equal to 2 and "s"=1, even though, especially in the presence of sterically voluminous ligands, "m" can also be limited to 1.

This preparation process of the sulfonic complexes included in formula (I) or their mixtures, can generally be conveniently carried out with $[Y]/[MX_1X_2X_3(X_4)_n]$ ratios ranging from 0.5 to 5.0, preferably from 1 to 2.5, depending on whether one, two or more sulfonic ligands are to be obtained per M atom. The possible excess of ligand, or residue of non-reacted ligand can usually be easily separated by precipitation or crystallization, and subsequent filtration, of the desired complex.

The solubility and stability characteristics towards atmospheric agents (humidity, oxygen) strongly depend on the X ligands present in the precursor $MX_1X_2X_3(X_4)_n$ as well as the type of Y sulfone used. This naturally influences the operating techniques and procedures for the separation from the reaction mixture and purification of the various complexes having formula (I), which experts in the field can adopt according to what is known in the art and which are described in the examples subsequently provided, without requiring any further inventive efforts or costs other than what is normally necessary for the setting up of a usual synthesis process.

Typical, non-limiting examples of sulfonic complexes of metals of group 4, included in formula (I) are the following:
$TiCl_4(Me_2SO_2)_2$, $TiCl_4(Et_2SO_2)_2$,
$TiCl_4(Ph_2SO_2)_2$, $[TiCl_4(Me_2SO_2)]_2$,
$TiBr_4(Me_2SO_2)_2$, $Ti(OMe)_4(Me_2SO_2)_2$,
$Ti(acac)Cl_3(Me_2SO_2)$, $ZrCl_4(Me_2SO_2)_2$,
$ZrCl_4(Ph_2SO_2)_2$, $[ZrCl_4(Et_2SO_2)]_2$,
$[ZrCl_4(Ph_2SO_2)]_2$, $ZrCl_4(Me)(Ph)SO_2$,
$ZrBr_4(Me_2SO_2)_2$, $ZrI_4(Me_2SO_2)_2$,
$Zr(NEt_2)_4(Me_2SO_2)_2$, $Zr[N(SiMe_3)_2]_2Cl_2(Me_2SO_2)$,
$Zr(OMe)_4(Me_2SO_2)_2$, $Zr(OPh)_2Cl_2(Me_2SO_2)_2$,
$Zr(OCOMe)_4(Me_2SO_2)$, $HfCl_4(Me_2SO_2)_2$,
$[HfCl_4(Ph_2SO_2)]_2$, $HfBr_4(Me_2SO_2)_2$.

Within the widest scope of the above formula (I) according to the present invention, when each symbol M, $X_1, X_2, X_3, X_4$ and Y represents two or more elements or ligands, they can have different independent meanings from each other. For example, the compound having the following structure is included in the above formula (I):

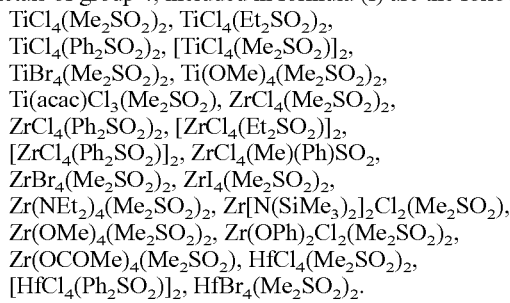

Component (B) of the catalytic composition according to the present invention comprises a sulfonic compound. As specified above, sulfonic compounds are organic compounds characterized by at least one $>SO_2$ group in which the sulfur atom is bonded to two carbon atoms. Component (B) may therefore consist of any sulfonic compound included in the sulfonic compounds previously defined as a possible ligand (Y) and, in particular, the sulfonic compounds according to formula (II) above.

The sulfonic compounds or their mixtures, in component (B), preferably have from 2 to 30, more preferably from 2 to 15 carbon atoms.

As specified above, component (C) of the catalytic composition according to the present invention essentially consists of an organic hydrocarbyl compound of a metal M' selected from the elements of Groups 1, 2, 12, 13 or 14 of the periodic table as defined above.

The elements C, Si and Ge are not considered metals according to the definition previously used. In particular, according to the present invention, said metal M' is selected from boron, aluminum, zinc, lithium, sodium, magnesium, gallium and tin, preferably aluminum and magnesium.

In a preferred embodiment of the present invention, component (C) is a hydrocarbyl compound of a metal of group 13, and is more preferably an aluminum compound represented by the following general formula (III):

$$Al(R_5)_pZ_q \quad\quad (III)$$

wherein:
each $R_5$ independently represents a linear or branched, saturated or unsaturated, cycloaliphatic or aromatic $C_1$-$C_{20}$ hydrocarbyl group, or a $C_1$-$C_{20}$ hydrocarbyl group substituted with one or more halogen atoms, preferably fluorine;
each Z independently represents a mono-anionic group containing at least one atom different from carbon directly bonded to the aluminum;
the indexes "p" and "q" can have any decimal numerical value ranging from 0 to 3 so that (p+q)=3 and "p" is equal to or higher than 0.5.

$R_5$ is preferably a hydrocarbyl group having from 1 to 8 carbon atoms, and even more preferably is a linear or branched alkyl group having from 1 to 6 carbon atoms, such as for example, methyl, ethyl, propyl, butyl, isobutyl.

Z is preferably hydride, halide, $C_1$-$C_{15}$ alkoxide, $C_1$-$C_{15}$ carboxylate, $C_2$-$C_{20}$ dialkyl-amide, $C_3$-$C_{30}$ trialkyl-silyl. The case in which Z is halide, especially chloride, is particularly preferred according to the present invention.

Furthermore, two or more groups independently selected from $R_5$ and Z in the compounds having formula (III) can be joined to each other to form a di- or polyvalent group, such as, for example, the tetramethylene group, or the divalent oxygen atom in oxygenated oligomeric derivatives of aluminum, generally known as aluminoxanes, which are included in the definition of component (C) of the catalyst according to the present invention, as claimed herein.

The indexes "p" and "q" preferably fall within the range of 1 to 2, extremes included. As is generally used in the empirical formula, when "s" and "q" do not have integer values, the compound having formula (III) consists of a mixture of compounds or is in the form of a dimer or trimer, as, for example, in the case of aluminum ethylses-quichloride, having the formula $AlEt_{1.5}Cl_{1.5}$.

Other examples of compounds represented by formula (III) include:
$AlMe_3$, $AlEt_3$, $Al(i-Bu)_3$, $AlMe_2Cl$, $AlEt_2Cl$, $AlEtCl_2$, $AlEt_{1.5}Cl_{1.5}$, $AlEt_2Br$, $AlEt_2I$, $AlMe_2F$, $Al(i-Bu)_2H$, $AlEt_2H$, $AlMe_2(OMe)$, $AlEt_2(OBu)$, $AlEt_2(OCOMe)$, $AlEt_2(OCOPh)$, $AlMe_2(NEt_2)$, $AlMe_2(NPh_2)$, $AlMe_2SiMe_3$.

The compounds having formula (III) are more preferably those wherein $R_5$ is methyl, ethyl, i-butyl and Z is chlorine or bromine; more preferably the compound (III) is $AlEt_2Cl$. The compounds having formula (III) can be used as component (C) alone or in a mixture of any two or more thereof.

The above catalyst according to the present invention can be prepared by simple contact and/or mixing of components (A), (C) and optionally (B), if present, as defined above, within a wide range of temperatures and pressures, preferably in the presence of an inert liquid medium. It can also be effected either outside the operating environment, i.e. more specifically outside the oligomerization reactor (preformed catalyst) or "in situ", i.e. inside the reactor, preferably in the same inert liquid medium used for oligomerizing the ethylene.

Pressures which can be conveniently used vary from the normal pressure, preferable for the preparation of the preformed catalyst, to the pressure used in the subsequent oligomerization of ethylene, i.e. up to about 7 MPa, in the case of preparation in situ. The preparation temperature of the catalytic composition preferably ranges from −30 to 80° C.

The order of addition of the components is not particularly critical. In the preformed catalytic system, it is more convenient for component (A) comprising the desired quantity of the compound of the metal M, either in pure form, in the solid or liquid state, or diluted in a suitable inert solvent, preferably the same in which component (C) is diluted, and component (B), if necessary, to be added to a solution of the hydrocarbyl organometallic compound (C) in a suitable inert solvent.

Said inert solvent is preferably selected from aromatic hydrocarbons, also partially halogenated, such as benzene, toluene, xylenes, mesitylene, chloro-benzene, fluoro-benzene, aliphatic hydrocarbons, such as pentane, hexane, heptane, octane, alicyclic hydrocarbons, such as cyclohexane, methylcyclohexane, or a mixture of any two or more thereof.

According to the present invention, the components (A), (B) and (C) may also, each independently, comprise an inert solid material with the function of carrier, preferably selected from organic and inorganic inert solids, generally used for the purpose in analogous oligomerization or polymerization processes of olefins such as, for example, alumina, silica, silico-aluminas, titania, zirconia, polystyrene. When used, this inert solid carrier preferably consists of from 40 to 90% by weight of the catalytic composition, excluding the weight of the possible solvent. Supporting methods are known to experts in the field, for example, by means of deposition and adsorption. According to a particular aspect, said supported catalytic composition can also be obtained by putting said carrier in contact with any two, or all three components (A), (B) and (C) contemporaneously during their reaction, or with the catalytic composition already preformed.

As specified above, components (A) and (B) in the present catalytic composition are in such proportions with each other that the S/M ratio ranges from 0 to 20, on the condition that S/M is equal to or greater than 0.5 when component (A) comprises only compounds of M without coordinated sulfonic groups. In the latter case, S/M preferably ranges from 1 to 10, more preferably from 1.5 to 5. Even more preferably, in this case, in the compound having formula (I), "m" is equal to 0 and the coordinating Y is absent.

According to another aspect of the present invention, in the preferred case in which component (A) comprises a compound having formula (I) in which Y is a sulfonic compound having formula (II) and "m" is at least 1, component (B) (i.e. the free sulfonic compound) is absent from the present composition.

The two components (A) and (C) are put in contact with each other and mixed in such quantities that the atomic ratio M'/M between the metal M' of component (C) and the metal M of component (A) ranges from 2 to 2000, preferably from 5 to 1000, even more preferably from 10 to 500.

The mixture thus obtained is catalytically active and can be used immediately or left to age, without undergoing substantial modifications in its characteristics, for times varying from a few minutes to a week. There are no particular temperature limitations for effecting the contact and reaction between the two components. This preferably ranges from −20° to 130° C., more preferably from 0 to 80° C., even more preferably 25° C. is selected.

The oligomerization process of ethylene, which forms another object of the present invention, comprises putting the above catalytic composition in contact, under oligomerization conditions, with ethylene, or a gas containing ethylene, preferably in the presence of a solvent and/or diluent, for a time sufficient to form the desired quantity of oligomers. In the preferred embodiment, a solvent/diluent is used, selected from aliphatic, aromatic and cycloaliphatic hydrocarbons, preferably having from 3 to 12 carbon atoms, more preferably from 4 to 8.

In another preferred embodiment of the present invention, the solvent/diluent is selected from one or more α-olefins, having from 4 to 26 carbon atoms, preferably having an even number of carbon atoms ranging from 4 to 26. More preferably, said solvent/diluent comprises, and even more preferably essentially consists of, a mixture of α-olefins having a number of carbon atoms greater than 10, particularly ranging from 10 to 26, which is obtained as a recycled product from the purification step of the reaction mixture after the removal of the light products ($C_4$-$C_8$).

The gas containing ethylene which can be used in the process of the present invention comprises an inert gas containing ethylene, preferably in a concentration of not less than 50% vol./vol., polymerization grade ethylene (for example high purity ethylene). In the preferred embodiment, the process of the present invention uses high purity ethylene.

The temperature and pressure of the oligomerization process of the present invention can be selected from those normally used in the art for analogous processes. In particular, the temperature advantageously ranges from 5 to 200° C., preferably from 20 to 150° C.; the pressure is normally lower than 10 MPa (pressure gauge), preferably from 0.05 to 7 MPa, even more preferably from 0.2 to 4 MPa.

The contact time (essentially coinciding with the oligomerization reaction time), depending on the temperature, pressure and concentration according to procedures which can be easily empirically measured during the normal experiments necessary for setting up the process, generally ranges from 10 minutes to 10 hours, preferably from 30 minutes to 120 minutes.

According to a typical, non-limiting embodiment of the present invention, the catalytic composition and ethylene are charged into the reactor at the desired pressure, for example 3 MPa, and the pressure is kept constant during the oligomerization reaction.

The reaction products prevalently consist of 1-butene, 1-hexene and 1-octene and other higher linear α-olefins having an even number of carbon atoms; 1-hexene is prevalently obtained, together with surprisingly high quantities of 1-octene, with respect to what is so far known in the art. The quantity of undesired higher oligomers which inevitably form a by-product of the process is, in fact, significantly reduced, even if the process is carried out under low production conditions of 1-butene. Under the preferred pressure and temperature conditions, i.e. P ranging from 2 to 4 MPa and T ranging from 60° to 140° C., the process carried out in the presence of the catalytic composition according to the present invention allows an oligomerization product to be obtained, consisting of over 50% by weight of 1-hexene and 1-octene, the remaining percentage prevalently being 1-butene.

The α-olefins thus produced can be separated from the raw reaction product according to methods known to experts in the field, particularly by means of fractionated distillation. According to the present invention, a part of the olefins higher than Co formed as by-product, can be recycled to the reaction step and used as solvent of the reaction itself.

The following examples are provide for a better understanding of the present invention.

EXAMPLES

The analytical techniques and characterization methods listed and briefly described below were used in the following examples.

The characterization by means of FTIR spectroscopy was effected on a Nicolet spectrophotometer mod. 510.

The characterization by means of $^1$H-NMR spectroscopy, mentioned in the following examples, was effected on a nuclear magnetic resonance spectrometer mod. Bruker MSL-300.

The characterization by means of X-ray spectroscopy for the determination of the molecular structures of the complexes illustrated was effected on a Bruker diffractometer mod. AX SP4.

The quantitative analysis of the α-olefin mixtures was effected by means of gas chromatography with a Hewlett-Packard "Fisons" instrument mod. 9000 equipped with a "Pona" capillary column [50 m×0.2 mm×0.5 microns]. The calculation of the quantities of each single α-olefin was carried out using the coefficients obtained from calibrations effected with 1-butene, 1-hexene, 1-octene, 1-decene, 1-dodecene and 1-tetradecene respectively, (all products available on the market with purities >99%) in the presence of 1,3,5-trimethylbenzene (>99.8 Fluka) as internal standard.

The characterization of the products present in the reaction mixtures was effected by means of gaschromatography/mass spectrometry (GC-mass) using a Finnigan TSQ 700 instrument.

The elemental analysis was carried out with an ICP-OES "Thermo Jarrel Ash" IRIS ADVANTAGE instrument.

During the preparations described in the examples, the following commercial reagents were used:
zirconium tetrachloride ($ZrCl_4$) FLUKA
aluminum triethyl (TEA) ($AlEt_3$) ALDRICH
aluminum diethyl chloride (DEAC) ($AlEt_2Cl$) ALDRICH
aluminum ethyl dichloride (EADC) ($AlEtCl_2$) ALDRICH
dimethyl sulfone ($Me_2SO_2$) ALDRICH
diethyl sulfone ($Et_2SO_2$) ALDRICH
diphenyl sulfone ($Ph_2SO_2$) ALDRICH
tetrahydrothiophene-1,1-dioxide (sulfolane) ALDRICH
2,5-dihydrothiophene-1,1-dioxide (3-sulfolene) ALDRICH The reagents and/or solvents used and not mentioned above are those commonly adopted in laboratories and on an industrial scale and can be easily found at the usual commercial operators specialized in the field.

Preparative Example 1

Synthesis of zirconium tetrachloride bis-dimethylsulfone

3.69 g of $ZrCl_4$ (15.8 mmoles) and 120 ml of anhydrous $CH_2Cl_2$ are charged, under a nitrogen atmosphere, into a 250 ml tailed test-tube, equipped with a magnetic stirrer. 2.99 g of dimethyl sulfone (31.8 mmoles) dissolved in 40 ml of $CH_2Cl_2$ are added dropwise at room temperature to the suspension thus obtained. At the end of the addition over a period of about an hour, the mixture is left under stirring at room temperature for a further 2 hours. In this phase, an abundant white microcrystalline solid is formed, which is recovered by filtration. A further aliquot of product is recovered by adding 30 ml of hexane to the mother liquor and filtering the white crystalline solid precipitated, which is joined to the product previously obtained. The product thus obtained is washed with two portions (15 ml) of $CH_2Cl_2$ and dried under vacuum (10 Pa) for 6 hours. 5.98 g of a white crystalline solid are thus obtained, which, after analysis and characterization by means of IR and X-ray spectroscopy, proves to be essentially pure $ZrCl_4(Me_2SO_2)_2$ (IV), with an overall yield of 89%.

Elemental analysis: found (calculated) for $C_4H_{12}O_4Cl_4S_2Zr$: Cl, 33.4 (33.66); S, 14.9 (15.22); Zr, 21.4 (21.65)%. $^1$H-NMR ($C_2D_2Cl_4$, δ ppm rel. to TMS): 3.43 (6H, s)

Preparative Example 2

Synthesis of zirconium tetrachloride bis-diphenylsulfone

Following a similar procedure to that described in Example 1, 3.70 g of $ZrCl_4$ (15.9 mmoles), 100 ml of $CH_2Cl_2$ are charged into a 250 ml tailed flask, and 7.03 g of $Ph_2SO_2$ (32.2 mmoles) dissolved in 50 ml of $CH_2Cl_2$ are added to the suspension. At the end of the addition, a slightly turbid pale yellow solution is obtained, which is filtered to remove all of the insoluble material and 80 ml of hexane are then added. A white crystalline precipitate is thus formed, which is recovered by filtration, washed with two 20 ml portions of hexane and dried at reduced pressure (10 Pa). Operating in this way, 8.48 g of a white crystalline solid are obtained, which, after analysis and characterization by means of IR spectroscopy, proves to be essentially pure $ZrCl_4(Ph_2SO_2)_2$ (V), with an overall yield of 80%.

Elemental analysis: found (calculated) for $C_{24}H_{20}O_4Cl_4S_2Zr$: Cl, 20.8 (21.18); S, 9.1 (9.58); Zr, 13.0 (13.62)%. $^1$H-NMR ($C_2D_2Cl_4$, δ ppm rel. to TMS): 8.01 (8H, d); 7.66 (4H, t); 7.54 (8H, t).

Preparative Example 3

Synthesis of zirconium tetrachloride diphenylsulfone

Following a similar procedure to that described in Example 1, 5.52 g of $ZrCl_4$ (23.7 mmoles), 120 ml of $CH_2Cl_2$ are charged into a 250 ml tailed flask, and 5.01 g of $Ph_2SO_2$ (22.9 mmoles) dissolved in 40 ml of $CH_2Cl_2$ are added to the suspension. At the end of the addition, a suspension is obtained, containing an abundant white solid, which is left under stirring at room temperature for 2 h and the solvent is then completely removed at reduced pressure. The resulting solid is transferred to an extractor equipped with a porous septum and bubble cooler, and extracted in continuous for 12 h using tetrachloroethane as solvent. At the end of the extraction, a small aliquot of insoluble solid remains on the porous septum, whereas the product present in the mother liquor is precipitated by cooling the solution and adding 50 ml of hexane. The product thus obtained is recovered by filtration, washed with two 20 ml portions of hexane and dried under vacuum (10 Pa). 7.91 g of a white crystalline solid are thus obtained, which, after analysis and characterization by means of IR and X-ray spectroscopy, proves to be essentially pure $[ZrCl_4(Ph_2SO_2)]_2$ (VI), with an overall yield of 74%.

Elemental analysis: found (calculated) for $C_{12}H_{10}O_2Cl_4SZr$: Cl, 29.8 (31.42); S, 6.3 (7.10); Zr, 18.8 (20.21)%. $^1$H-NMR ($C_2D_2Cl_4$, δ ppm rel. to TMS): 8.25-7.45 (unsolved multiplets).

Preparative Example 4

Synthesis of zirconium tetrachloride diethylsulfone

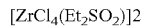
(VII).

Following a similar procedure to that described in Example 1, 3.57 g of $ZrCl_4$ (15.3 mmoles), 100 ml of $CH_2Cl_2$ are charged into a 250 ml tailed flask, and 1.81 g of $Et_2SO_2$ (14.8 mmoles) dissolved in 30 ml of $CH_2Cl_2$ are added to the suspension. At the end of the addition, a suspension is obtained, containing an abundant white solid, which is left under stirring at room temperature for 2 h and the reaction mixture is then transferred to an extractor equipped with a porous septum and bubble cooler, and the solid is extracted in continuous for 8 h with the same solvent used for the reaction. At the end of the extraction, a small quantity of insoluble solid remains on the porous septum, whereas the product present in the mother liquor is precipitated by cooling the solution and adding 50 ml of hexane. The solid thus obtained is recovered by filtration, washed with two 20 ml portions of hexane and dried under vacuum (10 Pa). 4.51 g of a white crystalline solid are thus obtained, which, after analysis and characterization by means of IR spectroscopy, proves to be essentially pure $[ZrCl_4(Et_2SO_2)]_2$ (VIII), with an overall yield of 83%.

Elemental analysis: found (calculated) for $C_4H_{10}O_2Cl_4SZr$: Cl, 38.9 (39.92); S, 8.5 (9.03); Zr, 25.3 (25.68)%. $^1$H-NMR ($C_2D_2Cl_4$, δ ppm rel. to TMS): 3.58 (4H, s); 1.61 (6H, s).

Examples 1-11

Oligomerization of Ethylene

Examples 1 to 11 below refer to a series of oligomerization tests of ethylene for the preparation of linear α-olefins according to the present invention, carried out using a preformed catalytic composition comprising one of the zirconium sulfonic complexes obtained as described above in preparative examples 1 to 4 as component (A), and diethyl aluminum chloride (DEAC) as component (C) (cocatalyst). In this case it is not necessary to add component (B) (free sulfone).

The specific conditions in each example and the results obtained are specified in Table I below, which indicates in succession, the reference example number, the complex used, the quantity of zirconium used, the atomic ratio between the aluminum in the DEAC and zirconium in the complex, the activity of the catalytic system expressed as grams of α-olefins per gram of metallic zirconium per hour: ($g_{ol}/g_{Zr}$.h), the quantity, expressed in weight percent, of the single α-olefins produced.

The oligomerization is carried out in an 0.5 litre pressure reactor, equipped with a magnetic drag anchor stirrer and external jacket connected to a heat exchanger for the temperature control. The reactor is previously flushed by maintaining under vacuum (0.1 Pascal) at a temperature of 80° C. for at least 2 hours.

180 g of anhydrous toluene (or other hydrocarbon solvent) are charged into the reactor, at 23° C., and optionally an aluminum alkyl or alkyl chloride in such a quantity as to form a solution having a concentration ranging from $1·10^{-4}$ to $1·10^{-3}$ M, having the function of scavenger. The reactor is then brought to the desired polymerization temperature and "polymerization grade" gaseous ethylene is fed by means of a plunged pipe until the desired total equilibrium pressure is reached, as specified, for each example in Table (I) below.

The DEAC, generally as an 0.8 M solution (as Al) in toluene, and the desired quantity of one of the above sulfonic complexes, in solid form or as a toluene solution/suspension having a concentration generally ranging from $3~10^{-3}$ to $5·10^{-2}$ M, are charged into a suitable tailed test-tube, maintained under nitrogen. The catalytic composition in solution thus formed is kept at room temperature for a few minutes and is then transferred under a stream of inert gas to a metal container from which, due to an overpressure of nitrogen, it enters the reactor.

The catalytic composition, consisting of the mixture of DEAC/sulfonic complex, can if necessary be left to age without losing its activity and selectivity, as described, for illustrative but non-limiting purposes, in Examples 9 and 10 for a period of 24 hours at room temperature, and in Example 11 for an hour at 60° C.

The polymerization reaction is carried out at the desired temperature indicated in Table (I), care being taken to keep the total pressure constant by continuously feeding ethylene to compensate the part which has reacted in the meantime. After 60 minutes, the ethylene feeding is interrupted and the polymerization is stopped by the addition of 10 ml of ethyl alcohol. After bringing the temperature of the reaction mixture to 20° C., a sample of the solution is removed, by means of a tap situated at the bottom of the reactor, and gas-chromatographic analyses are effected to determine the quantity and type of olefins formed. After eliminating the overpressure of ethylene, the autoclave is opened and its contents are poured into a suitable glass container, containing 500 ml of ethyl alcohol in order to determine the coagulation of possible polymeric products which, if present, are separated from the liquid phase dried at 60° C., at a reduced pressure of 1000 Pa, for at least 8 hours and finally weighed. The overall results are indicated in Table I below.

Examples 12 to 14 (Comparative)

Examples 12 to 14 (comparative) were essentially carried out under the same operating conditions as the previous example 1, but using a catalytic composition consisting of zirconium compounds and complexes known in the art as catalyst components for the oligomerization of ethylene.

The particular conditions, details and results obtained are indicated in Table I below.

The complexes zirconium tetrachloride-(dimethoxyethane) [$ZrCl_4(DME)$], used in Example 14, and zirconium tetrachloride-bis(tetrahydrofuran) [$ZrCl_4(THF)_2$], used in Example 13, were obtained in accordance with the procedure described in Comprehensive Coordination Chemistry, Pergamon Press, volume 3 (1997) pages 403-406.

TABLE I oligomerization of ethylene according to Examples 1 to 14[a].

| Ex. Nr. | Compl./ example | [Zr] moles · $10^{-3}$ | Al/Zr mol/mol | Activity $g_{ol}/g_{Zr} \cdot h$ | $C_4$ % w. | $C_6$ % w | $C_8$ % w | $C_{10}$ % w | $C_{12+}$ % w |
|---|---|---|---|---|---|---|---|---|---|
| 1 | (IV)/1 | 0.25 | 9.7 | 660 | 22.4 | 38.8 | 23.0 | 9.7 | 6.0 |
| 2 | (V)/2 | 0.18 | 10.0 | 230 | 17.8 | 39.0 | 25.9 | 11.0 | 6.4 |
| 3 | (VII)/4 | 0.21 | 19.2 | 1291 | 28.3 | 36.3 | 20.2 | 8.9 | 6.4 |
| 4 | (VII)/4 | 0.10 | 54.2 | 2687 | 28.7 | 35.8 | 20.9 | 8.9 | 5.8 |
| 5 | (VII)/4 | 0.052 | 108 | 6600 | 27.5 | 34.8 | 21.3 | 9.6 | 6.9 |
| 6 | (VI)/3 | 0.11 | 14.8 | 1464 | 24.7 | 33.0 | 21.5 | 11.2 | 9.7 |
| 7 | (VI)/3 | 0.048 | 117 | 4328 | 29.1 | 35.7 | 21.3 | 9.6 | 5.8 |
| 8 | (VI)/3 | 0.024 | 233 | 6376 | 33.0 | 37.6 | 18.3 | 7.2 | 4.0 |
| 9[b] | (IV)/1 | 0.25 | 9.9 | 770 | 25.1 | 36.7 | 22.3 | 9.4 | 6.4 |
| 10[b] | (V)/1 | 0.18 | 10.0 | 105 | 21.8 | 37.5 | 25.5 | 10.7 | 4.5 |
| 11[c] | (IV)/1 | 0.22 | 17.7 | 777 | 24.0 | 34.2 | 22.0 | 10.8 | 9.0 |
| 12 | $ZrCl_4$ | 0.11 | 14.6 | 1839 | 13.2 | 24.8 | 22.1 | 15.3 | 24.6 |
| 13 | $ZrCl_4(THF)_2$ | 0.056 | 14.3 | 8460 | 12.5 | 24.7 | 22.7 | 15.8 | 24.1 |
| 14 | $ZrCl_4(DME)$ | 0.066 | 14.5 | 511 | 14.0 | 30.0 | 24.1 | 13.8 | 18.2 |

[a]Each example was effected at a temperature of 80° C. and an ethylene pressure equal to 3.0 MPa;
[b]the catalytic composition was aged at 25° C. for 24 h;
[c]the catalytic composition was aged at 60° C. for 1 h.

Examples 15-28

Oligomerization of Ethylene in the Presence of a Catalytic Composition Comprising a Sulfone as Component (B)

Examples 15 to 28 refer to a series of oligomerization tests of ethylene for the preparation of linear α-olefins, carried out using a catalytic composition consisting of $ZrCl_4$, a sulfone as defined in general formula (II) and DEAC. The specific conditions in each example and the results obtained are specified in Table II below, which indicates in succession, the reference example number, the type of sulfone used, the quantity of zirconium used, the atomic ratio between the aluminum in the DEAC and zirconium, the molar ratio between the sulfone and zirconium, the type of procedure used for the preparation of the catalytic composition, the activity of the catalytic system expressed as grams of α-olefins per gram of metallic zirconium per hour: ($g_{ol}/g_{Zr} \cdot h$), the quantity, expressed in weight percentage, of the single α-olefins produced.

The oligomerization is carried out in an 0.5 litre pressure reactor, equipped with a magnetic drag anchor stirrer and external jacket connected to a heat exchanger for the temperature control. The reactor is previously flushed by maintaining under vacuum (0.1 Pascal) at a temperature of 80° C. for at least 2 hours.

180 g of anhydrous toluene (or other hydrocarbon solvent) are charged into the reactor, at 23° C., and optionally an aluminum alkyl or alkyl chloride in such a quantity as to form a solution having a concentration ranging from $1 \cdot 10^{-4}$ to $1 \cdot 10^{-3}$ M, having the function of scavenger. The reactor is then brought to the desired polymerization temperature and "polymerization grade" gaseous ethylene is fed by means of a plunged pipe until the desired total equilibrium pressure is reached, as specified, for each example in Table (II) below.

The preparation of the catalytic system can be effected according to any of the procedures described hereunder.

Procedure (i):

The following products are charged in order into a suitable tailed test-tube, maintained under nitrogen: the desired quantity of $ZrCl_4$ as a solid or as a toluene suspension having a nominal concentration generally ranging from $3 \cdot 10^{-3}$ to $5 \cdot 10^{-2}$ M, the desired quantity of sulfone, either pure or as a toluene solution having a concentration ranging from $5 \cdot 10^{-3}$ to $8 \cdot 10^{-2}$ M, and finally DEAC, generally as an 0.8 M solution (as Al) in toluene. The catalyst solution thus formed is kept at room temperature for a few minutes and is then transferred under a stream of inert gas to a metal container from which, due to an overpressure of nitrogen, it enters the reactor.

Procedure (ii):

The following products are charged in order into a suitable tailed test-tube, maintained under nitrogen: the desired quantity of $ZrCl_4$ as a solid or as a toluene suspension having a nominal concentration generally ranging from $3 \cdot 10^{-3}$ to $5 \cdot 10^{-2}$ M, DEAC, generally as an 0.8 M solution (as Al) in toluene, and finally the desired quantity of sulfone, either pure or as a toluene solution having a concentration ranging from $5 \cdot 10^{-3}$ to $8 \cdot 10^{-2}$ M. The catalyst solution thus formed is kept at room temperature for a few minutes and is then transferred under a stream of inert gas to a metal container from which, due to an overpressure of nitrogen, it enters the reactor.

Procedure (iii):

The following products are charged in order into a suitable tailed test-tube, maintained under nitrogen: DEAC, generally as an 0.8 M solution (as Al) in toluene, the desired quantity of sulfone, either pure or as a toluene solution having a concentration ranging from $5 \cdot 10^{-3}$ to $8 \cdot 10^{-2}$ M, and finally the desired quantity of $ZrCl_4$ as a solid or as a toluene suspension having a nominal concentration generally ranging from $3 \cdot 10^{-3}$ to $5 \cdot 10^{-2}$ M. The catalyst solution thus formed is kept at room temperature for a few minutes and is then transferred under a stream of inert gas to a metal container from which, due to an overpressure of nitrogen, it enters the reactor.

The catalytic composition obtained according to any of the procedures (i), (ii) and (iii), can be left to age for 24 hours at room temperature, or at 60° C. for 1 h.

The oligomerization reaction is carried out at the desired temperature, care being taken to keep the total pressure constant by continuously feeding ethylene to compensate the part which has reacted in the meantime. After 60 minutes, the ethylene feeding is interrupted and the polymerization is stopped by the addition of 10 ml of ethyl alcohol. After bringing the temperature of the reaction mixture to 30° C., a sample of the solution is removed, by means of a tap situated at the bottom of the reactor, and gas-chromatographic analyses are effected to determine the quantity and type of olefins formed. After eliminating the overpressure of ethylene, the autoclave is opened and its contents are poured into a suitable glass container, containing 500 ml of ethyl alcohol in order to determine the coagulation of possible polymeric products which, if present, are separated from the liquid phase dried at 60° C., at a reduced pressure of 1000 Pa, for at least 8 hours and finally weighed. The overall results are indicated in Table II below.

TABLE II oligomerization of ethylene according to examples 15-28.

| Ex. Nr. | Sulfone (B) | [Zr] mol·$10^{-3}$ | Al/Zr mol/mol | (B)/Zr mol/mol | Proc. | Activity $g_{ol}/g_{Zr}·h$ | $C_4$ % w. | $C_6$ % w | $C_8$ % w | $C_{10+}$ % w |
|---|---|---|---|---|---|---|---|---|---|---|
| 15 | $Et_2SO_2$ | 0.052 | 38.4 | 1 | (i) | 4572 | 30.3 | 35.1 | 20.2 | 14.4 |
| 16 | $Et_2SO_2$ | 0.052 | 38.4 | 2 | (i) | 3051 | 31.8 | 35.2 | 19.9 | 13.1 |
| 17 | $Et_2SO_2$ | 0.049 | 48.9 | 4 | (i) | 2686 | 33.1 | 34.8 | 19.0 | 13.1 |
| 18 | $Et_2SO_2$ | 0.049 | 48.9 | 10 | (i) | 2184 | 34.2 | 36.2 | 18.7 | 10.9 |
| 19 | $Et_2SO_2$ | 0.049 | 38.4 | 4 | (ii) | 2412 | 31.0 | 35.8 | 19.6 | 13.6 |
| 20 | $Et_2SO_2$ | 0.049 | 38.4 | 4 | (iii) | 2294 | 34.7 | 35.1 | 18.3 | 11.9 |
| 21 | $Ph_2SO_2$ | 0.046 | 34.8 | 4 | (i) | 1282 | 31.9 | 38.0 | 19.2 | 10.9 |
| 22 | $Ph_2SO_2$ | 0.039 | 41.0 | 10 | (i) | 858 | 39.7 | 35.9 | 16.7 | 7.7 |
| 23 | Sulfolene | 0.046 | 34.8 | 1 | (i) | 5684 | 25.5 | 35.3 | 21.1 | 18.0 |
| 24 | Sulfolene | 0.046 | 34.8 | 4 | (i) | 2456 | 33.0 | 35.3 | 18.6 | 13.1 |
| 25 | Sulfolane | 0.046 | 34.8 | 1 | (i) | 7266 | 30.4 | 35.4 | 20.3 | 13.7 |
| 25 | Sulfolane | 0.046 | 34.8 | 4 | (i) | 3817 | 29.3 | 36.4 | 19.9 | 14.5 |
| 27 | Sulfolane | 0.046 | 34.8 | 10 | (i) | 1540 | 37.7 | 34.2 | 17.1 | 11.0 |
| 28[b] | Sulfolane | 0.046 | 34.8 | 4 | (i) | 3599 | 35.8 | 32.6 | 18.4 | 13.3 |

[b]$P_{ethylene}$ = 2.0 MPa

Each example was carried out at a temperature of 80° C. and an ethylene pressure equal to 3.0 MPa

The invention claimed is:

1. A process for the oligomerization of ethylene to produce prevalently linear α-olefins having 4, 6 and 8 carbon atoms, comprising contacting ethylene, or a gas comprising ethylene, with a catalytic composition comprising the following components: (A) a compound of zirconium having the following formula (Ia):

$$[MX_1X_2X_3X_4Y_m]_s \quad (Ia)$$

wherein M is zirconium in oxidation state +4;

wherein $X_1$, $X_2$, $X_3$, and $X_4$ each independently represent any organic or inorganic anionic ligand, bonded to the Metal M as an anion in an ionic couple or with a covalent bond;

wherein each Y represents a neutral organic ligand coordinated to the metal M by means of a heteroatom selected from non-metallic atoms of groups 15 or 16 of the periodic table;

wherein "m" represents the number of neutral Y ligands, optionally coordinated to M and can have any integer or decimal value ranging from >0 to ≦3; and wherein each Y represents a sulfonic compound having the following formula (II):

(II)

wherein $R_3$ and $R_4$, the same or different, each independently represent a linear or branched, saturated or unsaturated, cycloaliphatic or aromatic $C_1$-$C_{20}$ hydrocarbyl group, a $C_1$-$C_{20}$ hydrocarbyl group substituted with one or more halogen atoms, or a $C_1$-$C_{20}$ hydrocarbyl group comprising one or more heteroatoms of Groups 14 to 16 of the periodic table of elements, and furthermore, $R^3$ and $R^4$ can be joined to each other to form a saturated or unsaturated, $C_4$-$C_{20}$ cyclic structure, comprising the sulfur atom of the sulfonic group, said structure optionally containing one or more of the heteroatoms;

wherein "s" has integer values ranging from 1 to 6;

(B) an organic compound of formula (II) comprising at least one sulfonic group (>$SO_2$) bonded to two carbon atoms;

(C) a hydrocarbyl organometallic compound of a metal M' selected from the group consisting of boron, aluminum, zinc, lithium, sodium, magnesium, gallium and tin;

the components (A), (B) and (C) being in such a quantity that the atomic ratios respectively of the metal M in (A), of the sulfur S in the sulfonic group of (B) and of the metal M' in (C), respect the following proportions:

S/M=(from 0 to 20)/1

M'/M=(from 2 to 2000)/1, wherein an oligomerization product is obtained, consisting of over 50% by weight of 1-hexene and 1-octene.

2. The process according to claim 1, wherein said oligomerization of ethylene is carried out at a temperature ranging from 5° C. to 200° C. and at a pressure lower than 10 MPa (pressure gauge).

3. The process according to claim 2, wherein said oligomerization of ethylene is carried out at a temperature ranging from 20° C. to 150° C. and a pressure ranging from 0.05 MPa to 7 MPa.

4. The process according to any one of claims 1 to 3, wherein said oligomerization is carried out in the presence of a material selected from the group consisting of a solvent, a diluent, or a combination thereof.

5. The process according to claim 4, comprising said material, wherein said material is selected from the group consisting of aliphatic hydrocarbons, aromatic hydrocarbons, cycloaliphatic hydrocarbons, and combinations thereof.

6. The process according to claim 1, wherein said catalytic composition is preformed before contact with ethylene.

7. The process according to claim 1, wherein said catalytic composition is formed in situ, by the contact of components (A), (C) and, optionally, (B), in the presence of ethylene.

8. The process according to claim 1, wherein said catalytic composition is formed by putting in contact and reacting components (A) and (B) to form a product, and reacting the product thus obtained with component (C) to form the catalytic composition.

9. The process according to claim 1, wherein said catalytic composition is formed by putting in contact and reacting components (A) and (C) to form a product, and reacting the product thus obtained with component (B) to form the catalytic composition.

10. The process according to claim 1, wherein said catalytic composition is formed by putting in contact and reacting components (C) and (B) to form a product, and reacting the product thus obtained with component (A) to form the catalytic composition.

11. The process according to claim 1, further comprising, after said contacting, at least a separation step of said α-olefins having 4, 6 and 8 carbon atoms.

12. The process according to claim 11, wherein said separation step produces, as by-product, a mixture of linear α-olefins having from 10 to 26 carbon atoms.

13. The process according to claim 12, wherein said mixture of linear α-olefins having from 10 to 26 carbon atoms is partly recycled and used as the material in the oligomerization step of said process.

14. The process according to claim 1, wherein, in said compound having formula (Ia), said ligands X ($X_1$, $X_2$, $X_3$ or $X_4$) are independently selected from chloride, bromide, a hydroxide group, a hydrogen-carbonate group, a nitrate group, a nitrite group, a —$NR_1R_2$ amide or a —$PR_1R_2$ phosphide group, wherein $R_1$ and $R_2$ are each hydrogen or an alkyl or aryl group having from 1 to 20 carbon atoms, optionally bonded to each other to form a cyclic structure comprising the nitrogen or phosphorus atom, a linear or branched alkoxide group, having from 1 to 10 carbon atoms, a group deriving from carboxylate, carbamate or xanthate organic acids, having from 1 to 10 carbon atoms, a linear or branched alkylsulfide group, a linear, cyclic or branched hydrocarbyl group, having from 1 to 15 carbon atoms, optionally also comprising one or more halogen atoms different from chlorine, an anionic diketonate or ketoester group having up to 15 carbon atoms, or two or more of the above ligands $X_1$, $X_2$, $X_3$ or $X_4$ can be aggregated with each other to represent a polyvalent ligand, or a cyclic structure comprising the metal M and having from 5 to 15 atoms in the cycle.

15. The process according to claim 1, wherein "m" ranges from 1 to 3.

16. The process according to claim 15, wherein said S/M ratio between the sulfur S in the sulfonic group of component (B) and the metal M in component (A), is equal to 0.

17. The process according to claim 1, wherein, in said sulfonic compound having formula (II), said $R_3$ and $R_4$ are two saturated or unsaturated, aliphatic groups, each having from 1 to 6 carbon atoms, or they are joined to form a saturated or unsaturated, cyclic structure having from 5 to 8 atoms in the cycle, including the sulfur atom.

18. The process according to claim 1, wherein said hydrocarbyl organometallic compound of M' is selected from compounds included in the following general formula (III): Al($R_5$)$_p$$Z_q$ wherein: each $R_5$ independently represents a linear or branched, saturated or unsaturated, cycloaliphatic or aromatic $C_1$-$C_{20}$ hydrocarbyl group, or a $C_1$-$C_{20}$ hydrocarbyl group substituted with one or more halogen atoms; each Z independently represents a mono-anionic group comprising at least one atom different from carbon directly bonded to the aluminum; the indexes "p" and "q" can have any decimal numerical value ranging from 0 to 3 so that (p+q)=3 and "p" is equal to or higher than 0.5.

19. The process according to claim 18, wherein, in said formula (III): $R_5$ is a linear or branched alkyl group having from 1 to 6 carbon atoms, Z is selected from hydride, halide, $C_1$-$C_{15}$ alkoxide groups, $C_1$-$C_{15}$ carboxylate groups, $C_2$-$C_{20}$ dialkyl-amide groups, $C_3$-$C_{30}$ trialkyl-silyl groups, or two groups independently selected from $R_5$ and Z can be joined to form a divalent group bonded to the aluminum atom, the indexes "p" and "q" are range from 1 to 2.

20. The process according to claim 19, wherein, in said formula (III), Z is chloride.

21. The process according to claim 1, wherein said component (C) consists of an aluminoxane.

22. The process according to claim 1, wherein the proportions between components (A) and (C) of said composition are such that the ratio M'/M ranges from 2 to 2000.

23. The process of claim 1, wherein the catalytic composition employed in the process consists of components (A), (B), and (C).

24. The process of claim 1, wherein Y is sulfolane.

25. The process of claim 1, wherein at least one of $R_3$ and $R_4$ is a $C_1$-$C_{20}$ hydrocarbyl group comprising one or more heteroatoms selected from the group consisting of Si, O, N, S, and P.

* * * * *

UNITED STATES PATENT AND TRADEMARK OFFICE
CERTIFICATE OF CORRECTION

| | | |
|---|---|---|
| PATENT NO. | : 8,198,497 B2 | Page 1 of 1 |
| APPLICATION NO. | : 10/497537 | |
| DATED | : June 12, 2012 | |
| INVENTOR(S) | : Paolo Biagini et al. | |

It is certified that error appears in the above-identified patent and that said Letters Patent is hereby corrected as shown below:

On the title page, Item (87), the PCT Pub. Date is incorrect. Item (87) should read:

-- (87)   PCT Pub. No.:     WO/2003/053573
           PCT Pub. Date:    Jul. 3, 2003 --

Signed and Sealed this
Thirty-first Day of July, 2012

David J. Kappos
*Director of the United States Patent and Trademark Office*